United States Patent [19]
Lane et al.

[11] Patent Number: 5,145,674
[45] Date of Patent: * Sep. 8, 1992

[54] BIOLOGICALLY-ACTIVE COMPOUNDS COMPRISING A BIOLOGICALLY-ACTIVE ANIONIC PORTION AND A WATER-INSOLUBLE, INORGANIC CATIONIC PORTION

[75] Inventors: George A. Lane; Harold E. Rossow, both of Midland, Mich.

[73] Assignee: The Dow Chemical Company, Midland, Mich.

[ * ] Notice: The portion of the term of this patent subsequent to Sep. 6, 2005 has been disclaimed.

[21] Appl. No.: 693,838

[22] Filed: Apr. 30, 1991

[51] Int. Cl.$^5$ .................... A61K 31/74; A61K 31/60; A61K 31/19
[52] U.S. Cl. ................. 424/78.08; 424/78.1; 514/165; 514/570
[58] Field of Search .............. 424/78, 79, 78.08

[56] References Cited

U.S. PATENT DOCUMENTS

| | | | |
|---|---|---|---|
| 3,879,525 | 4/1975 | Miyata et al. | 423/277 |
| 4,000,100 | 12/1976 | Baldyga | 260/23 X |
| 4,008,193 | 2/1977 | Scheidl et al. | 260/23 X |
| 4,221,687 | 9/1980 | Minagawa et al. | 260/23 X |
| 4,269,744 | 5/1981 | Hulyalkar et al. | 260/23 X |
| 4,299,759 | 11/1981 | Miyata et al. | 260/45.7 R |
| 4,326,961 | 4/1982 | Lee et al. | 210/683 |
| 4,371,656 | 2/1983 | Kashiwase et al. | 524/443 |
| 4,392,979 | 7/1983 | Lee et al. | 252/184 |
| 4,392,980 | 7/1983 | Lee et al. | 252/184 |
| 4,446,201 | 5/1984 | Lee et al. | 428/696 |
| 4,501,840 | 2/1985 | Werle et al. | 524/387 |
| 4,540,727 | 9/1985 | Vogdes . | |
| 4,661,282 | 4/1987 | Clark | 252/179 |
| 4,722,938 | 2/1988 | Sunshine et al. | 514/479 |
| 4,769,079 | 9/1988 | Clark | 423/467 |
| 4,769,080 | 9/1988 | Clark et al. | 106/402 |
| 4,773,936 | 9/1988 | Clark et al. | 106/402 |
| 4,840,676 | 6/1989 | Clark | 423/467 |
| 4,877,620 | 10/1989 | Loew et al. | 424/451 |

FOREIGN PATENT DOCUMENTS 5249258 10/1975 Japan .

OTHER PUBLICATIONS

Noncondensed Aromatic Compounds, Aluminum Acetysalicylate, 1963, col. 13898.
Noncondensed Aromatic Compounds, Basic Aluminum Salts of Acetylsalicylic Acid and a Nontoxic Water-Soluble Acid, 1964, col. 461.
Benzene Derivatives, Monohydroxyaluminum Bis-(acetylsalicylate), 1960, col. 16430.
Essential Oils and Cosmetics, Basic Aluminum Compounds (in cosmetics), 1963, col. 7314.
Chemical Abstracts, The Bioavailability of Asprin from Asprin Aluminum, 1982, p. 372.
Derwent Publications, Ltd., Production of Stabilizing Agent for Chlorine-Containing Resin, 1988, J6-30-17-950-A.
Ind. Eng. Chem. Prod. Res. Dev., Pharmaceutical Aspects of Clay-Organic Interactions, 1983, pp. 665-671.

Primary Examiner—Thurman K. Page
Assistant Examiner—Raj Bawa

[57] ABSTRACT

A biologically-active compound which includes an inorganic mixed metal cationic portion having anion exchange properties and an anionic portion containing a biologically-active anion. The mixed metal cationic portion can be an oxide, hydroxide, or both, and can be fully hydrated, partially hydrated, or not hydrated. The biologically-active anion can be, e.g., an antibiotic, an analgesic, an antimicrobial, a pharmaceutical, an antioxidant, or an agricultural chemical such as a herbicide or a pesticide. These biologically-active compounds can have controlled-release properties and can be produced by relatively simple processes, using for the cationic portion relatively common starting materials. These biologically-active compounds are useful, for example, in compositions to form pharmaceuticals, antioxidants, or herbicides, and can be incorporated into a polymeric material to form a shaped body, such as a plastic film which can be utilized to form bags for food storage or transportation. Also included are processes for making the biologically-active compounds.

8 Claims, No Drawings

BIOLOGICALLY-ACTIVE COMPOUNDS COMPRISING A BIOLOGICALLY-ACTIVE ANIONIC PORTION AND A WATER-INSOLUBLE, INORGANIC CATIONIC PORTION

TECHNICAL FIELD

This invention relates generally to biologically-active mixed metal compounds, compositions containing the compounds, and methods for preparing the compounds.

BACKGROUND OF THE INVENTION

One of the great accomplishments of modern chemical science has been the discovery of a multitude of chemical compounds that are biologically-active toward man or other animals, plants, or micro-organisms. A "biologically-active" material is one that acts upon an organism, or one of its parts or systems, to produce a physiological effect. Many of these materials have found utility in fostering human well-being or comfort. For example, pharmaceuticals are useful in promoting health or alleviating afflictions in man and domestic or other animals. Some of the pharmaceuticals, e.g., antibiotics, act by controlling harmful microorganisms. Other pharmaceuticals, e.g., analgesics, act on a system of an organism to reduce pain.

Other biologically-active compounds are useful in furthering disease-free growth of plants, such as crops, ornamental plants, trees, and lawn grass. Some biologically-active compounds act against infective agents and others operate on the systems of the plant organisms to control the infective agents.

Useful biologically-active compounds are also employed to control organisms that cause harm or discomfort to humans or other animals or plants. For example, insecticides are used to eradicate disease-spreading vectors such as malaria-carrying mosquitos; herbicides are employed to control weeds on crop land; and fungicides or antioxidants are applied to foods to retard spoilage.

While these biologically-active chemicals have benefitted mankind enormously, their use has been accompanied with problems in application. For example, drugs taken orally or by injection ordinarily do not release the active ingredient evenly over time. However, it is nearly always desirable to have a constant level of a drug supplied to the body over the period of treatment. When a conventional medicinal tablet or capsule is taken, the serum drug concentration rises rapidly to a peak that is higher than the therapeutic range, i.e., the range in which the drug concentration suffices to produce the desired therapeutic effect. Concentrations above the therapeutic range can be toxic and/or can produce adverse side effects. With time, the serum drug concentration decreases into the therapeutic range, perhaps remaining at the desired level for a hour or two, eventually dropping to a level where the drug is pharmacologically ineffective. When the next dose is taken, the cycle is repeated.

To mitigate these problems, sustained-release and controlled- release technology has been the subject of considerable effort. In sustained-release techniques, the delivery of the drug is extended over a much longer period. This allows medications to be taken less often, which is more convenient for the patient, with less chance of inadvertently missing a dose. However, the problem of uneven delivery of the medication remains.

In controlled-release techniques, the rate of delivery to the body is controlled so as to be more uniform over a prolonged period. Controlled-release properties provide all the advantages of sustained-release properties, and also minimize toxic side effects.

Numerous sustained-release techniques have been developed in an attempt to control the kinetics of drug release. These techniques include coating tablets with slow-dissolving coatings, converting drugs to salts with low solubility, compressing tablets to high density, and converting medications to suspensions or emulsions. For example, in U.S. Pat. No. 3,350,270 to William E. Gaunt, sustained-release is claimed by enveloping a drug in a film of aluminum acetylsalicylate, optionally combined with a film-forming polymer.

Another system for sustained-release, widely used today, employs a capsule containing hundreds of tiny beads consisting of a core of medication coated with wax layers of varying thickness. The drug is released, depending on the depth of the coating on the individual beads, from a few minutes to 12 hours or more, to prolong the effect of the medication.

Progress also has been made in developing controlled-release technology. One approach utilizes a "reservoir", which is a drug body surrounded by a non-biodegradable polymer. Release of the drug depends on diffusion through the polymer. An example of such a reservoir is the closed silicone rubber tube containing a contraceptive drug, which has been designed to be implanted in the body. Organic cation exchange resins have also been used to provide a "reservoir" effect In U.S. Pat. No. 2,990,332, J. W. Keating discloses cationic drugs, e.g., ephedrine, complexed with sulfonic acid cation exchange resins. The medication is said to be released slowly, at an even rate, as metal cations in the gastrointestinal tract exchange with the cationic drugs in the complex.

Controlled-release can also be obtained from "matrix" devices. In these devices, the drug is dispersed in a polymeric matrix, rather than encapsulated in a polymer. Medication release is controlled by diffusion of the drug through the matrix. In a variation of this technique, a slowly-decomposable or erodible polymer is employed, and medication is released as the polymer decomposes or erodes. In addition, certain drugs can be chemically attached to polymer chains, and released by cleavage of the polymer-drug bond by hydrolysis or enzyme action.

Yet another broad area of controlled-release technology involves the use of water as a solvent to release medications. This can be done by creating osmotic pressure to expel a drug solution from a capsule, or by swelling the capsule contents to enhance diffusion.

In spite of the many developments cited, improvements in controlled-release technology are needed to simplify the products, make them more economical, and to improve their delivery properties.

Another problem in taking oral medications is that the drug can be released in the wrong internal location for optimum action. Thus, many drugs taken orally are compounded with complicated coatings to prevent absorption high in the digestive tract and to release the drug later at a more appropriate location.

Yet another difficulty with oral medications is that almost all medications have an unpleasant taste. This is ameliorated by employing coated tablets, capsules, and the like. While this improves palatability, it can also add to the cost.

Yet another problem with some oral medications, such as analgesics, is irritation to the digestive tract. Buffering of the analgesic should aid in preventing irritation. Presently, many buffered analgesic compositions are mixtures of a pain- killing drug with basic metal oxides, hydroxides, or carbonates. Some of these additives are incompatible with the drug. For example, $Mg(OH)_2$ reacts with acetylsalicylic acid, causing it to decompose and become less effective. Some buffered aspirin formulations separate the drug from the buffering additives with elaborate layered designs, requiring complicated processes to make the products.

Sustained-release and controlled-release technology is also desirable in agricultural applications for biologically-active compounds. When selective herbicides are applied to crops or lawns, control of undesirable plants is achieved by applying the herbicide onto the leaf or stem surfaces of the weed and maintaining it in place until enough herbicide has been absorbed to destroy the plant. If rain occurs shortly after application, the biologically-active compound can be washed away, hydrolyzed, or otherwise dissipated, requiring one or more additional applications.

Subsequent growth of new weeds can be prevented by applying certain herbicides to the soil to inhibit seed sprouting or kill small seedlings as they emerge. The duration of effectiveness in this case is limited by the persistence of the herbicide in the soil. Rain or soil moisture can wash away, dissolve, or hydrolyze the active ingredient.

Many of the measures previously discussed for achieving sustained-release or controlled-release of drugs have been tried for agricultural chemicals, such as herbicides. However, except for very specialized applications, the added cost is prohibitive. Coating, pelletizing, or encapsulation can be effective in prolonging herbicide action. However, in addition to the added costs, these techniques often retard the absorptive process and hamper delivery of an effective dose. Therefore, most of these techniques, by their nature, result in delayed release, followed by a release surge of the active material, and then steadily decreasing levels of active material. Therefore, frequent re- application of herbicide is often necessary.

Other applications for biologically-active compounds relate to the food industry. Frozen or refrigerated fruits, vegetables, meats, and other perishable foodstuffs become, after a period of time, less palatable by oxidation from air permeating the food package. Spoilage can be retarded by using protective packaging, for example, plastic film food storage bags fabricated from materials having low gas permeability such as vinylidene copolymers. Plastic film food storage bags are useful for prolonging storage life, but even the measurably low permeability of the storage bags allows entry of atmospheric gases which can ruin the food by discoloration or rancidity.

Chemical antioxidant compounds are useful in retarding such food spoilage. While some antioxidants can be mixed with the food, this usually is not desirable, since the taste or color can be altered. Also, there is much concern over the safety of food additives in general. One means of circumventing this problem is to incorporate an antioxidant directly into the packaging material, e.g., the plastic film. This is difficult, however, as the antioxidants most frequently used are at least partially volatilized during film fabrication processes, which usually are performed at high temperatures.

While biologically-active compounds of the type discussed above are of enormous benefit, there are impediments to their use, outlined above, which limit their application. The utilization of many of these biologically-active compounds could be improved if means were available to alter the mode and/or rate of release or delivery.

Although sundry inorganic materials have been discovered which have cation exchange capabilities, there are few with anion exchange capabilities. In U.S. Pat. No. 3,002,932, Duwell and Shepard reported a non-crystalline anion exchanger based on mixed hydrated oxides of a pair of metals (Al, Si, Ti, Zn, Zr) in which the atom percentage of the metal of lower valency is 3 to 99 times that of the higher valent metal. The higher valent cation is balanced with a bound anion.

In U.S. Pat. No. 3,879,525 Miyata and co-inventors recite a hydrated composite metal hydroxide of magnesium with Al, Fe, or Cr with a variety of inorganic anions to balance the cation of higher valency.

Lee and Bauman, in U.S. Pat. No. 4,326,961, disclose a method of removing anions from solution using mixed inorganic oxides of the formula $Mg(OH)_2.nAl(OH)_3.mH_2O$. The same inventors, in U.S. Pat. Nos. 4,392,979, 4,392,980, and 4,446,201 disclose crystalline aluminates of the chemical formula $MgA_a{}^yZ_b{}^y.nAl(OH)_3.mH_2O$ with A and Z being hydroxide, halide, inorganic acid, or organic acid anions.

In U.S. Pat. No. 4,661,282, which patent is hereby incorporated by reference, Clark reveals a high temperature anion exchange material of the structure $\{M^1{}_{(1-x)}Q^{(1+1)}{}_xO_y(OH)_z\}(A^{-1})_d(A^{-2})_o(A^{-3})_f(A^{-4}).nH_2O$ with limits on x, n, y, z, d, e, f, g, 2y+z, and d+2e+3f+4g, where M and Q are metal ions and $A^{-1}$, $A^{-2}$, $A^{-3}$, and $A^{-4}$ are exchangeable anions. Materials of this invention can be used as starting materials for producing the biologically-active compounds of the present invention.

In U.S. Pat. No. 4,769,079, which patent is hereby incorporated by reference, Clark, et. al., expand this technology to disclose compositions in which the insoluble mixed metal hydrated oxide ion exchange material is complexed with a water-soluble dye anion to form a water-insoluble pigment.

Burba and Strother, in U.S. Pat. No. 4,990,268, disclose compositions of matter, useful as components in well drilling fluids, of the chemical formula $Li_mD_d$-$T(OH)_{(m+2d+3+na)}A^n{}_a$ in which D is a specified divalent metal ion (including Mg); T is a trivalent metal ion (including Al); A is an anion other than OH; and there are limits on m, d, m+d, na, and (m+2d+3+na). A preferred composition is $MgAl(OH)_{4.7}Cl_{0.3}$. The latter material can be used as a starting material for producing the biologically-active compounds of the present invention.

Therefore, it is a primary objective of the present invention to provide biologically-active compounds which are simple in form and are made by simple, economical processes, as well as being compounds which also have controlled-release capabilities.

In one aspect of the invention, it is an object to provide a controlled-release oral medication which is substantially insoluble in saliva and is substantially soluble under the conditions found lower in the digestive tract, such as the acidic conditions found in the stomach, or the anion-rich conditions of the intestinal tract. It is another object of this aspect of the invention to provide an oral medication which causes reduced irritation of the digestive tract relative to many current medications. Further, it is another object of this aspect of the invention to provide an oral medication which has flavor-masking capabilities without requiring coating or encapsulation of the compound.

In yet another aspect of the invention, it is an object to provide an antioxidant to reduce the spoilage rate of foods, especially those foods stored in plastic bags at room, refrigeration, or freezing temperatures. It is another object of the present invention to provide an antioxidant which is capable of being formulated into plastic film, e.g., food storage bag films, and which is substantially non-volatile at hot-film fabrication temperatures.

In another aspect of the invention, it is an object to provide a herbicide which is substantially insoluble in water and resistant to rain, so that there is less need for reapplication after unfavorable weather.

It is still another object of this aspect of the invention to provide a herbicide with controlled-release capability to exterminate weeds and provide a residual activity to prevent later germination or growth of weeds.

In other aspects of the invention, the objects are to provide biologically-active compositions containing the biologically-active compounds and methods for preparing the biologically-active compounds.

SUMMARY OF THE INVENTION

In accordance with the preferred embodiment of the invention, these and other objects and advantages are addressed as follows.

In accordance with the present invention, there are provided water-insoluble, biologically-active compounds that are formed of two portions: (1) an inorganic cationic portion having anionic exchange properties, which are comprised of mixed metal oxides and/or hydroxides and (2) an exchangeable anion or anions, at least one of which is biologically-active. The term "mixed metal" refers to a combination of two different metals.

More particularly, the present invention provides a biologically-active compound, comprising a compound having the chemical formula $$M^1{}_{1-x}Q^{a+1}{}_xO_y(OH)_zA^{-1}{}_dA^{-2}{}_eA^{-3}{}_fA^{-4}{}_g \cdot n\, H_2O$$

wherein M is a metal element having a positive valence of a, Q is a metal element having a positive valence of $a+1$; $A^{-1}$, $A^{-2}$, $A^{-3}$, and $A^{-4}$ are each one or more exchangeable anions having a valence of $-1$, $-2$, $-3$, and $-4$, respectively, at least one of the exchangeable anions being a biologically-active anion; a is 2, 3, 4, or 5; x is greater than zero and less than or equal to about 0.5; y, z, d, e, f, and g are each greater than or equal to zero; $2y+z$ is equal to a; $d+2e+3f+4g$ is greater than zero and less than or equal to x; and n is greater than or equal to zero and less than or equal to about 10. The invention also provides compositions containing the biologically-active compounds and processes for producing the biologically-active compounds disclosed herein.

DETAILED DESCRIPTION OF THE INVENTION

The present invention generally includes water-insoluble, biologically-active compounds that are formed of two portions: (1) an inorganic cationic portion having anion exchange properties, which is formed of mixed metal oxides and/or hydroxides; and (2) an exchangeable anion or anions, at least one of which is biologically-active.

The biologically-active anion can be derived from, for example, the salt or acid of an antioxidant, a pharmaceutical such as an antibiotic, an analgesic, or an antimicrobial, or an agricultural chemical such as a herbicide or a pesticide. Examples of pesticides include insecticides, fungicides, acaricides, rodenticides, and nematicides. More specifically, the biologically-active anion can be selected from, among others, 2-(4-isobutylphenyl) propionate, acetylsalycilate, 2,4-dichlorophenoxy acetate, or ascorbate. The biologically-active compound has the capability of delivering a biologically-active material to a desired site.

The mixed metal cationic portion has an excess positive charge, due to substitution of a metal of higher valence into a compound of a metal of lower valence. The excess positive charge is balanced by the negative charge of an exchangeable anion or anions. When two or more exchangeable anions are employed, the anions can be selected from biologically-active and biologically-non-active anions, so long as at least one exchangeable anion of the compound is biologically-active. An exchangeable anion of the compound is firmly incorporated in the lattice structure of the compound, and remains until the exchangeable anion is replaced by another anion.

A representative biologically-active compound of the present invention has the following general formula:

$$M^a{}_{1-x}Q^{a+1}{}_xO_y(OH)_zA^{-1}{}_dA^{-2}{}_eA^{-3}{}_fA^{-4}{}_g \cdot n\, H_2O$$

wherein M is a metal element having a positive valence of a, Q is a metal element having a positive valence of $a+1$; $A^{-1}$, $A^{-2}$, $A^{-3}$, and $A^{-4}$ are each one or more exchangeable anions having a valence of $-1$, $-2$, $-3$, and $-4$, respectively, and wherein at least one of the exchangeable anions is biologically-active; a is 2, 3, 4, or 5; x is greater than zero and less than or equal to about 0.5; y, z, d, e, f, and g are each equal to or greater than zero; $2y+z$ is equal to a; $d+2e+3f+4g$ is greater than zero and less than or equal to x; and n is greater than or equal to zero and less than or equal to about 10.

In the above formula, the metal element or elements M can be divalent, trivalent, quadrivalent, or pentavalent. The metal element or elements Q can be trivalent, quadrivalent, pentavalent, or hexavalent.

If metal element M is divalent, it can be selected from, for example, magnesium, calcium, strontium, barium, iron, zinc, tin, copper, cobalt, manganese, nickel, cadmium, lead, mercury, and mixtures thereof.

If metal element M or Q is trivalent, it can be selected from, for example, aluminum, iron, cobalt, nickel, chromium, bismuth, antimony, yttrium, lanthanum, cerium, scandium, gallium, rhenium, indium, and mixtures thereof.

If metal element M or Q is quadrivalent, it can be selected from, for example, titanium, germanium, tin, lead, zirconium, hafnium, vanadium, and mixtures thereof.

If metal element M or Q is pentavalent, it can be selected from, for example, phosphorus, arsenic, antimony, molybdenum, tungsten, vanadium, niobium, tantalum, and mixtures thereof.

If metal element Q is hexavalent, it can be selected from, for example, chromium, molybdenum, tungsten, and mixtures thereof.

However, in this invention, the metal element M is preferably magnesium or aluminum, and the metal element Q is either aluminum or titanium.

Another aspect of the present invention entails providing the biologically-active compound with controlled-release properties, for example, the capability of modifying the release of the biologically-active material, i.e., accelerating or retarding the rate of release of the biologically-active material from the biologically-active compound, or altering the location or environment of the release.

The rate and site of delivery of the biologically-active anion from the compounds of this invention can be determined by controlling the release of the biologically-active anion from the compounds. This control of release can be accomplished in several ways, for example, by changing the pH of the medium, or by introducing anionic species which displace the biologically-active anion from the compound.

As an example of retarding the rate of release of the biologically-active material, a herbicide solution applied to lawns or agricultural fields is soon dissipated by solution in rainwater. Conversely, a compound of the invention which incorporates a herbicidal anion is substantially insoluble in water, and therefore resistive to dissolution by rain after application. The herbicidal anion can be released from the compound by being exchanged slowly, over time, by other anions in the soil at the application site. The compound of the invention thus acts as a dispensing reservoir of biologically-active material.

As an example of altering the location or environment of the release of a biologically-active material, a drug tablet, taken orally, can begin to dissolve in the mouth, losing some of its effectiveness, and leaving the patient with an unpleasant taste. A compound of the invention which incorporates the same drug as an anion can be substantially insoluble in saliva, and yet dissolve rapidly in the acidic environment of the stomach. In a similar way, a medication which acts most expeditiously when absorbed in the intestines can be incorporated as an anion in a compound of the invention, designed to resist dissolution in the saliva of the mouth or the acidic stomach environment, and yet release medication by anion exchange in the anionic-rich environment of the intestine.

One method of obtaining this modification of rate, location, or environment of release of the biologically-active anion is to use a biologically-non-active anion, either as a part of the anionic portion of the biologically-active compound or simply admixed with the biologically-active compound as a salt of the biologically-non-active anion.

As an example of the use of a biologically-active compound admixed with a biologically-non-active anion source, the biologically-active compound can be formulated with auxiliary compounds, for example, the salt of a biologically-non-active anion which is more strongly attracted to the mixed metal cationic portion than the biologically-active anion The rate of release of biologically-active material is accelerated as long as there is a sufficient concentration of biologically-non-active anions to displace the biologically-active anions from the biologically-active compound. This technique can be used to provide an initial, fast release of active material, followed by a slower, measured release.

With respect to the use of a biologically-non-active anion incorporated as a part of the anionic portion of a biologically-active compound, if the biologically-non-active anion is more strongly attracted to the mixed metal cationic portion than the biologically-active anion, exchange of proximate anions will be more rapid with the biologically-active anion than with the biologically-non-active anion, and the release of the biologically-active material will be enhanced. Conversely, if the biologically-non-active anion is less strongly attracted to the mixed metal cationic portion than the biologically-active anion, exchange of proximate anions will be more rapid with the biologically-non-active anion than with the biologically-active anion, thereby retarding the release of the biologically-active material. If the biologically-active and biologically-non-active anions are approximately equally attracted to the mixed metal cationic portion, then both will exchange at approximately equal rates with proximate anions.

Typically, the larger the negative valence of the anion, the more attracted it is to the positively-charged mixed metal cationic portion. Therefore, if the biologically-active anion is monovalent, then divalent, trivalent, or quadravalent anions will exchange more rapidly with the mixed metal cationic portion and tend to displace the biologically-active anion. In the same way, trivalent or quadravalent anions tend to displace divalent biologically-active anions.

However, for each example of the invention, there is a unique set of anion exchange properties. For example, in a compound of the present invention in which M is magnesium and Q is aluminum, it will be seen that a sulfate ion $SO_4^=$ is much more strongly attracted to the cationic portion than a carbonate ion, $CO_3^=$, although both are divalent. Thus, by selection of the biologically-active and biologically-non-active anions, and of the metal elements M and Q, a range of release properties can be attained.

The biologically-non-active exchangeable anion can be selected from any inorganic or organic exchangeable anions commonly known in the art of anion exchangers. Examples of biologically-non-active anions suitable for the invention include halide, hydroxide, nitrite, nitrate, phosphate, carbonate, sulfate, permanganate, sulfonate, and carboxylate. For the purposes of the present invention, halide is considered to include oxyhalide; phosphate includes dihydrogen phosphate, hydrogen phosphate, acid phosphate, diphosphate, and pyrophosphate; carbonate includes bicarbonate; sulfate includes bisulfate; and carboxylate includes acetate, formate, maleate, stearate, and benzoate and the like.

The biologically-non-active anions of the same valence may be mixtures of two or more exchangeable anions. For example, the anion $A^{-2}$ may be a combination of two or more exchangeable anions described above, such as a mixture of sulfate and carbonate The biologically-active compounds of the invention may also employ the combination of two or more exchangeable anions of different valences, aside from the biologically-active anion, such as chloride ($Cl^{-1}$) and carbonate ($CO_3^{-2}$).

In one embodiment of the invention, the biologically-active compound utilizes the antioxidant capabilities of ascorbic acid A representative compound is represented by the formula:

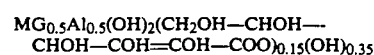

$MG_{0.5}Al_{0.5}(OH)_2(CH_2OH—CHOH—CHOH—COH=COH—COO)_{0.15}(OH)_{0.35}$

This new compound has the antioxidant capabilities of ascorbic acid, which is widely used to prevent discoloration and retard spoilage in foodstuffs. The compound further has the advantage of low volatility which allows it to be incorporated into food storage plastic film, which is typically prepared at high temperatures.

One method of incorporating the antioxidant compound in such a polymeric material is to admix the compound in dry powdered form into the polymeric material to form a biologically-active composition. The compound can be mixed, for example, by melt-blending, with pellets or granules of either a thermoplastic or thermoset resin at the time of processing. Because of the significant thermal stability of the compounds of the present invention, a number of processing methods can be employed, including injection molding, compression molding, vacuum forming, blow molding, structural foam molding (including conventional low pressure, high pressure and expanding molding using either chemical or physical blowing agents), extrusion (including profile, pipe, wire and cable, sheets and co-extrusion), co-injection molding, and thermoforming.

A representative compound of the invention which uses an analgesic anion as the biologically-active anion, namely, acetylsalicylate, is represented by the formula:

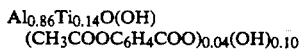

$Al_{0.86}Ti_{0.14}O(OH)(CH_3COOC_6H_4COO)_{0.04}(OH)_{0.10}$

This compound combines the analgesic properties of acetylsalicylic acid, also known as "aspirin", with the added properties of buffering, flavor masking, and controlled-release The compound is quite insoluble at the pH of saliva, but will dissolve in the stomach where the pH is markedly lower Such an acetylsalicylate-containing compound is best prepared when one of the metal elements is not magnesium, as magnesium compounds can cause the acetylsalicylate ion to decompose to salicylic acid and acetic acid, decreasing its effectiveness as an analgesic.

Another representative compound of the invention which uses an analgesic anion, 2-(4-isobutylphenyl) propionate, is represented by the formula:

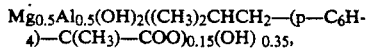

$Mg_{0.5}Al_{0.5}(OH)_2((CH_3)_2CHCH_2—(p—C_6H_4)—C(CH_3)—COO)_{0.15}(OH)_{0.35}$

This new compound combines the analgesic properties of 2(4-isobutylphenyl)propionic acid, also known as ibuprofen, with the advantages as discussed above for the aspirin-containing compound. Other ibuprofen-type drugs suitable as the biologically-active anion in this manner can be found in U.S. Pat. No 4,722,938, which patent is hereby incorporated by reference.

To use the analgesic-containing compounds of this invention, the compounds can be formulated into any of several types of oral medications. For example, the compounds can be formed into tablets with additives such as colorants, flavorings, and processing aids, e.g., binders, such as starch.

A representative compound of the invention. which uses a herbicidal anion, namely, 2,4-dichlorophenoxy acetate, as the biologically-active anion is represented by the formula:

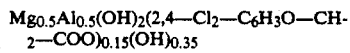

$Mg_{0.5}Al_{0.5}(OH)_2(2,4—Cl_2—C_6H_3O—CH_2—COO)_{0.15}(OH)_{0.35}$

This new compound has herbicidal activity similar to that of 2,4-dichlorophenoxyacetic acid or its salts or esters. In addition, this compound is quite insoluble in water, and, therefore, will resist dissolution or hydrolysis after application in the field. The unchanged compound then will constitute a reservoir of herbicide to be released steadily at the application or translocation site, controlling weed species and preventing sprouting of seeds. The release of the active herbicide anion occurs through movement of other anions in the soil to the application site, where they exchange with the herbicide anion, 2,4-dichlorophenoxyacetate, in the compound. With proper formulation, the herbicide is released, after application, at a slow, controllable rate, thus requiring fewer applications per growing season. In case rain should occur shortly after spraying, the water insolubility of this compound prevents premature dissolution and retards hydrolysis of the herbicide anion. Herbicidal compositions containing the above compound may include additives to facilitate application such as wetting agents and viscosity modifiers.

The representative compositions mentioned hereinabove may be said to have the general chemical formula:

$M^1{}_{1-x}Q^{a+1}{}_xO_y(OH)_zA^{-1}{}_d \cdot nH_2O$ wherein M is a metal element having a positive valence of a and being selected from either magnesium or aluminum, Q is a metal element having a positive valence of $a+1$ and being selected from either aluminum or titanium; $A^{-1}$ is one or more exchangeable anions having a valence of $-1$, at least one of the exchangeable anions being selected from 2-(4-isobutyphenyl) propionate, acetylsalicylate, ascorbate, and 2,4-dichlorophenoxy acetate; a is 2 or 3; x is greater than zero and less than or equal to about 0.5; y and z are each greater than or equal to zero; $2y + z$ is equal to a; d is greater than zero and less than or equal to x; and n is greater than or equal to zero and less than or equal to about 10.

Generally, the compounds of the present invention can be prepared in several ways. The invention provides an in situ process in which a mixture of water and a metal source compound is admixed with a mixture of water and a biologically-active anion source compound. The metal source compound may be one or more compounds which contain the metals selected to form the metal part of the mixed metal cationic portion. The biologically-active anion source compound contains the biologically-active anion. When admixed, the two source compounds form the biologically-active compound in situ.

In the in-situ process for producing the biologically-active compound, aqueous solutions or suspensions of the metal source compounds are added, either simultaneously or sequentially, to a pH-adjusted aqueous solution or suspension of a biologically-active anion source compound, forming the biologically-active compound. Optionally, the biologically-active product formed can be isolated at this point by separating the water-soluble reaction products from the water-insoluble biologically-active compound by filtration and washing or the material can be processed or formulated further without separation. Also, the separated product optionally can be dried, processed further, or formulated in the wet state.

Alternatively, in a second process, the compounds of the invention may be formed by contacting (a) a biologically-non-active anion source compound containing a mixed metal cationic portion and a biologically-non-active anion with (b) a biologically-active anion source compound containing a biologically-active anion to allow at least partial exchange of the biologically-active anion for the biologically-non-active anion of the biologically-non-active anion source compound, thereby forming the biologically-active compound containing the mixed metal cationic portion and the biologically-active anion.

The biologically-non-active anion source compound containing the mixed metal cationic portion can be prepared or obtained from another source. For the case in which it is prepared, the biologically-non-active anion source compound can be produced by admixing, at a selected pH, a mixture of water and a metal source compound with a mixture of water and a biologically-non-active anion source compound. The metal source compound contains the metals selected to form the metal part of the mixed metal cationic portion of the biologically-active compound, and the biologically-non-active anion source compound contains the biologically-non-active anion. When admixed, the source compounds form a biologically-non-active mixed metal compound which may then be removed from the admixed mixtures by filtration and washing techniques and optionally dried.

Compounds suitable as the biologically-non-active anion source compounds containing mixed metal cationic portions are also disclosed in U.S. Pat. No. 4,661,282, 4,769,079 and 4,990,268, which are hereby incorporated by reference.

Compounds which may be used to supply the metal and, optionally, the non-biologically-active anion, in the above processes include, for example, metal chlorides or alkali metal aluminates. In the case where the constituent metals are magnesium and aluminum, solutions of magnesium chloride and sodium aluminate can be used. The reaction:

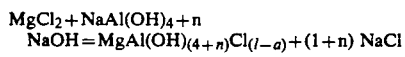

can take place. In this case, the pH of the solution has been adjusted by addition of sodium hydroxide.

In the case where the constituent metals are aluminum and titanium, solutions of sodium aluminate and titanium tetrachloride can be used. The reaction:

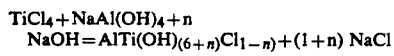

can take place. Again, the pH of the solution has been adjusted by addition of sodium hydroxide. Alternatively, aluminum chloride may be used as the source of the aluminum in making these types of compounds.

Preferably, the metal source compounds in the above-described processes include a first metal source compound selected from either magnesium chloride and aluminum chloride and a second metal source compound selected from either sodium aluminate and titanium tetrachloride.

The above-described preparation techniques are similar to those known in the art, for example, those described in U.S. Pat. Nos. 4,661,282 and 4,773,936, which patents are hereby incorporated by reference.

Thus, there are provided, in accordance with the present invention, biologically-active materials which are simple in form and made by simple, economical processes, and which also have controlled-release capabilities.

Provided by another aspect of the invention is a controlled-release oral medication which (1) is substantially insoluble in saliva and substantially soluble under the conditions found lower in the digestive tract, such as the acidic conditions found in the stomach, or the anion-rich conditions of the intestinal tract, (2) causes reduced irritation of the digestive tract relative to many current medications, and (3) has flavor-masking capabilities without requiring coating or encapsulation of the compound.

Provided by another aspect of the invention is an antioxidant to reduce the spoilage rate of foods and is capable of being formulated into plastic film, e.g., food storage bag films.

Provided by another aspect of the invention is a herbicide which is substantially insoluble in water and resistant to rain and has controlled-release capability.

In addition, useful compositions containing the biologically-active compounds of the invention and methods of preparing the compounds are provided by this invention.

The following examples are illustrative only and should not be construed as limiting the invention which is properly delineated in the appended claims.

EXAMPLES

Example 1

Solution A was prepared by dissolving 75.0 g $MgCl_2 6H_2O$ in 200 ml deionized water Solution B was prepared by adding 18 g of 50 wt% aqueous NaOH solution and 40.6 g sodium aluminate to 200 ml deionized water. Solution C was prepared by dissolving 29.6 g of aqueous 50 wt% NaOH and 22.8 g 2-(4-isobutylphenyl) propionic acid in 800 ml deionized water, and had a measured pH of 13.09. To adjust the pH to 10.5, 18 drops of concentrated HCl and 15 ml of 1N HCl was then added.

Approximately equal amounts of Solutions A and B were added to pH-adjusted Solution C at 27.8° C. while stirring. The rates of addition of Solutions A and B to Solution C were controlled to maintain a pH of about 10.5 in the mixture. After 50 minutes, all of Solution A had been added, 15 ml of Solution B remained, and the pH was 10.54. The remaining 15 ml of Solution B was then added, and the mixture was stirred for an additional 110 minutes. The pH of the mixture was then 10.74. The pH was adjusted to 10.5 with aqueous HCl. The reaction product was filtered and washed three times with 70° C. deionized water. The reaction product was then dried overnight in a 70° C. air circulating oven. The product yield was 73.3 g.

The product, analyzed by liquid chromatography, UV spectroscopy, and Karl Fischer analysis, contained 28 wt% 2-(4-isobutylphenyl) propionate and 11.8 wt% water. Thus, the sample contained 31.75 wt% of analgesic on a dry basis. This corresponds closely with the theoretical analysis of the compound:

$Mg_{0.5}Al_{0.5}(OH)_2((CH_3)_2CHCH_2-(p-C_6H_4)-C(CH_3)-COO)_{0.15}(OH)_{0.35}$, which contains 31.95 wt% 2-(4-isobutylphenyl) propionate. The product is useful as an analgesic.

Example 2

Solution A was prepared by slow addition of 11 ml (19 g) TiCl$_4$ to 190 ml water to form a clear solution, followed by addition of 145 g AlCl$_3$6H$_2$O and sufficient water to make 300 ml of aqueous solution. Solution B was prepared by adding 170 g of a 50 wt% aqueous NaOH solution to enough water to make 300 ml of solution. Solution C was prepared by dissolving 19.0 g acetylsalicylic acid in 8.4 g of 50 wt% aqueous NaOH solution and enough water to make one liter. To adjust the pH to 9.0, 16 g 1N aqueous NaOH was added to Solution C.

Solutions A and B were combined together slowly, with stirring. Next, 37 g 1N aqueous NaOH was added to the mixture. After completion of the addition, the material was allowed to react for 45 minutes, and then the solid precipitate was filtered off and washed with deionized water until the filtrate analyzed for less than 0.1 ppm Na$^+$.

Half of the filtrate prepared was slurried in solution C, heated to 55° C., and stirred for 1.5 hours. To adjust the pH to 9.0, 26 g 1N aqueous NaOH was added to the slurry. The resulting precipitate was filtered off. Analysis of the final filtrate indicated a product with the approximate formula:

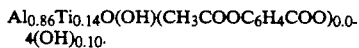

Al$_{0.86}$Ti$_{0.14}$O(OH)(CH$_3$COOC$_6$H$_4$COO)$_{0.04}$(OH)$_{0.10}$.

The product is useful as an analgesic.

EXAMPLE 3

Solution A was prepared by adding sufficient deionized water to 112.5 g MgCl$_2$6H$_2$O to make 200 ml of aqueous solution Solution B was prepared by adding sufficient deionized water to a mixture of 60.9 g sodium aluminate trihydrate and 16.0 g of a 50 wt% aqueous NaOH solution to make 200 ml of aqueous solution Solution C was prepared by adding 13.1 g of a 50 wt% aqueous NaOH solution and 29.6 g ascorbic acid to 800 ml deionized water and adjusting the pH to 9.0 by adding 0.5 g of 1N aqueous NaOH solution.

Equal amounts of Solutions A and B were added simultaneously to Solution C, with stirring, the rate of addition being slow enough to assure dispersion of the added solutions. After completion of the addition, the mixture was allowed to react for one-half hour, and then the water-soluble reaction products were removed by filtration and a double washed with deionized water. The product was analyzed, and found to contain, on a dry basis, a mixture of approximately one-third Mg$_{0.5}$Al$_{0.5}$(OH)$_2$Cl$_{0.15}$(OH)$_{0.35}$, and two-thirds:

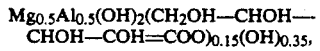

Mg$_{0.5}$Al$_{0.5}$(OH)$_2$(CH$_2$OH—CHOH—CHOH—COH=COO)$_{0.15}$(OH)$_{0.35}$,

The product is useful as an antioxidant.

Example 4

Solution A was prepared by adding sufficient deionized water to 75.0 g MgCl$_2$6H$_2$O to make 200 ml of aqueous solution Solution B was prepared by adding sufficient deionized water to a mixture of 40.6 g sodium aluminate trihydrate and 16.0 g of a 50 wt% aqueous NaOH solution to make 200 ml of aqueous solution Solution C was prepared by adding 9.0 g of a 50 wt% aqueous NaOH solution and 24.8 g 2,4-dichlorophenoxyacetic acid to 800 ml water and clarifying the resulting solution by filtration.

Equal amounts of Solutions A and B were added simultaneously to Solution C, with stirring, the rate of addition being slow enough to assure dispersal of the added solutions. As Solutions A and B were added, the pH was adjusted periodically to 10 by adding aqueous HCl or aqueous NaOH to the reaction mixture. After completion of the addition of Solutions A and B, the mixture was allowed to react one hour, and then the water-soluble reaction products were removed by filtration and double washed with deionized water. Analysis of the product indicated, on a dry basis, 7.2% of unreacted 2,4-dichlorophenoxyacetic acid, 25.2% of Mg$_{0.5}$Al$_{0.5}$(OH)$_2$Cl$_{0.15}$(OH)$_{0.35}$, 6.5% Mg(2,4-Cl$_2$—C$_6$H$_3$O—CH$_2$—COO)$_2$, and 52.1% of MG$_{0.5}$Al$_{0.5}$(OH)$_x$(2,4—Cl$_2$—C$_6$H$_3$O—COO)$_{0.15}$(OH)$_{0.35}$, all the percentages being based on weight. The product is useful as a herbicide.

Example 5

Cranberry beans (Phaseolus vulgaris) were planted in soil and allowed to grow to the second trifoliate stage. Experimental groups of the plants were then sprayed at a rate of 374 liters per hour for a total of 40 gallons per acre equivalent with six different dilutions to give applications ranging from 4.4 to 140 acid equivalents per hectare, using: 1) a standard 2,4-D ester herbicide, 2) a standard 2,4-D alkanolamine salt herbicide, and 3) an aqueous suspension of the product prepared in Example 4, buffered to pH values of 4, 7, or 10 Plant mortality or damage was essentially the same for each of the agents, 1), 2), or 3), indicating that the product of Example 4 is effective at controlling weeds.

While our invention has been described in terms of a few specific embodiments, it will be appreciated that other embodiments could readily be adapted by one skilled in the art. Accordingly, the scope of our invention is to be considered limited only by the following claims.

We claim:

1. A biologically-active compound, comprising a biologically-active analgesic anion and a water-insoluble, inorganic cationic portion which contains two different metals, the cationic portion having anion exchange properties.

2. A biologically-active compound having the chemical formula:

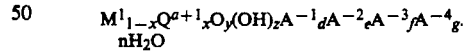

$$M^1{}_{1-x}Q^{a+1}{}_xO_y(OH)_zA^{-1}{}_dA^{-2}{}_eA^{-3}{}_fA^{-4}{}_g \cdot nH_2O$$

wherein M is a metal element having a positive valence of a,

Q is a metal element having a positive valence of a+1,

A$^{-1}$, A$^{-2}$, A$^{-3}$, A$^{-4}$, are each exchangeable anions having a valence of −1, −2, −3, and −4, respectively, at least one of the exchangeable anions being an analgesic anion, a is 2, 3, 4, or 5, x is greater than zero and less than or equal to about 0.5, Y, z, d, e, f, and g are each greater than or equal to zero, 2Y+z is equal to a, d+2e+3F+4g is grater than zero and less than or equal to x, and n is greater than or equal to zero and less than or equal to about 10.

3. The biologically-active compound of claim 2, wherein M is selected from the group consisting of magnesium and aluminum and Q is selected from the group consisting of aluminum and titanium.

4. The biologically-active compound of claim 2 wherein the biologically-active anion is 2-(4-isobutylphenyl)propionate.

5. The biologically-active compound of claim 2, wherein the biologically-active anion is acetylsalicylate.

6. The biologically-active compound of claim 2, wherein the exchangeable anions include a biologically-non-active anion which has the capability of modifying the release of the biologically-active anion from the biologically-active compound.

7. The biologically-active compound of claim 6, wherein the biologically-non-active anion is selected from the group consisting of halides, hydroxides, nitrites, nitrates, phosphates, carbonates, sulfates, permanganates, carboxylates, and sulfonates.

8. A biologically-active compound having the chemical formula:

$$M^1{}_{1-x}Q^{a+1}{}_xO_y(OH)_zA^{-1}{}_d \cdot nH_2O$$

wherein M is a metal element having a positive valence of a and being selected from the group consisting of magnesium and aluminum, Q is a metal element having a positive valence of $a+1$ and being selected from the group consisting of aluminum and titanium, $A^{-1}$ is an exchangeable anion having a valence of $-1$ and includes an anion selected from the group consisting of 2-(4-isobutylphenyl) propionate and acetylsalicylate a is 2 or 3, x is greater than zero and less than or equal to about 0.5, y and z are each greater than or equal to zero, $2Y+z$ is equal to a, d is greater than zero and less than or equal to x, and n is greater than or equal to zero and less than or equal to about 10.

* * * * *

UNITED STATES PATENT AND TRADEMARK OFFICE
CERTIFICATE OF CORRECTION

PATENT NO. : 5,145,674

DATED : September 8, 1992

INVENTOR(S) : George A. Lane; Harold E. Rossow

It is certified that error appears in the above-identified patent and that said Letters Patent is hereby corrected as shown below:

Title should correctly read -- BIOLOGICALLY-ACTIVE COMPOUNDS COMPRISING A BIOLOGICALLY-ACTIVE ANIONIC PORTION AND A WATER-INSOLUBLE, INORGANIC CATIONIC PORTION (AS AMENDED)--.

Under U.S. PATENTS.
-- 3,002,932   10/1961   Duwell et al.
   3,238,163   3/1966    O'Neil, et al.
   3,350,270   10/1967   Gaunt --
should also be listed.

Under OTHER PUBLICATIONS

--Chemical Abstract, Aluminum Monohydroxy Bis (acetyl-salicylate) and Ethyl Acetoacetate, col 7436

Chemical Abstract, Organic Aluminum-Compounds with Controlled Rate of Hydrolysis, Vol. 61, col. 5572

Chemical Abstract, Blood Level and Analgesic Activity of Salicylic Acid Derivative, Vol 61, col. 9911

Derwent Publications, Antiblocking Agent for Ethylene, DD-207-550-A

Derwent Publications, Vinyl Chloride Resing Composition, J5-5142-043

Derwent Publications, halogen Containing Resin Stabilization, J6-1034-042-A

Special Report article, 1985, p. 30-48 --
should also be listed.

UNITED STATES PATENT AND TRADEMARK OFFICE
CERTIFICATE OF CORRECTION

PATENT NO. : 5,145,674

DATED : September 8, 1992

INVENTOR(S) : George A. Lane; Harold E. Rossow

It is certified that error appears in the above-identified patent and that said Letters Patent is hereby corrected as shown below:

In the claims:

Col. 14, line 50, the formula should correctly read -- $M^a{}_{1-x}Q^a$ --.

Col. 14, line 64, "Y, z,d,e,f" should correctly read -- y, z, d, e, f, and g --.

Col. 14, line 67, "3F+46 should correctly read -- $3f+4g$ --.

Col. 14, line 67, "grater" should correctly read -- greater --.

Col. 16, line 4, the formula should correctly read -- $M^a{}_{1-x}Q^a$ --.

Col. 16, line 20, 2Y+z should correctly read -- $2y+z$ --.

Signed and Sealed this

First Day of August, 1995

Attest:

BRUCE LEHMAN

Attesting Officer

Commissioner of Patents and Trademarks